(12) United States Patent
Wang et al.

(10) Patent No.: US 9,040,759 B2
(45) Date of Patent: *May 26, 2015

(54) PREPARATION OF FLUORINATED OLEFINS VIA CATALYTIC DEHYDROHALOGENATION OF HALOGENATED HYDROCARBONS

(75) Inventors: Haiyou Wang, Amherst, NY (US); Hsueh Sung Tung, Getzville, NY (US); Sudip Mukhopadhyay, Berkeley, CA (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1564 days.

This patent is subject to a terminal disclaimer.

(21) Appl. No.: 12/167,159

(22) Filed: Jul. 2, 2008

(65) Prior Publication Data

US 2009/0043136 A1    Feb. 12, 2009

Related U.S. Application Data

(60) Provisional application No. 60/958,468, filed on Jul. 6, 2007.

(51) Int. Cl.
| | | |
|---|---|---|
| C07C 21/18 | (2006.01) | |
| B01J 35/00 | (2006.01) | |
| B01J 27/10 | (2006.01) | |
| B01J 27/12 | (2006.01) | |
| B01J 27/138 | (2006.01) | |
| C07B 35/06 | (2006.01) | |
| C07C 17/25 | (2006.01) | |

(52) U.S. Cl.
CPC ............. B01J 35/0006 (2013.01); B01J 27/10 (2013.01); B01J 27/12 (2013.01); B01J 27/138 (2013.01); C07B 35/06 (2013.01); C07C 17/25 (2013.01)

(58) Field of Classification Search
None
See application file for complete search history.

(56) References Cited

U.S. PATENT DOCUMENTS

| | | | |
|---|---|---|---|
| 4,465,786 A | 8/1984 | Zimmer et al. | |
| 5,276,240 A | 1/1994 | Timmons et al. | |
| 7,230,146 B2 * | 6/2007 | Merkel et al. | 570/155 |
| 7,312,367 B2 * | 12/2007 | Tung et al. | 570/155 |
| 8,053,612 B2 * | 11/2011 | Wang et al. | 570/158 |
| 8,648,222 B2 * | 2/2014 | Wang et al. | 570/158 |
| 2005/0090698 A1 * | 4/2005 | Merkel et al. | 570/155 |
| 2007/0112230 A1 | 5/2007 | Mukhopadhyay et al. | |
| 2007/0129579 A1 * | 6/2007 | Wang et al. | 570/155 |
| 2007/0129580 A1 * | 6/2007 | Mukhopadhyay et al. | 570/155 |
| 2007/0197842 A1 | 8/2007 | Mukhopadhyay et al. | |

FOREIGN PATENT DOCUMENTS

| | | |
|---|---|---|
| WO | 2007079431 A2 | 7/2007 |
| WO | 2008040969 A2 | 4/2008 |

OTHER PUBLICATIONS

Burgin et al., "Unimolecular Reaction Kinetics of CF2ClCF2CH3 and CF2ClCF2CD3: Experimental Evidence for a Novel 1,2-FCl Rearrangement Pathway," Journal of Physical Chemistry. A, vol. 105, pp. 1615-1621 Nov. 2000, XP002448571 (US).
MX Examination Report, dated Jul. 1, 2013 regarding corresponding Mexican Patent Application No. MX/a/2009/013376.
Burgin, et al., "Unimolecular Reaction Kinetics of CF2ClCF2CH3 and CF2ClCF2CD3: Experimental Evidence for a Novel 1,2-FCl Rearrangement Pathway", J. Phys. Chem. A (2001), vol. 105, 1615-1621 (XP-002448571).
EP Examination report issued in EP08772398.7 dated Jun. 20, 2013.

* cited by examiner

*Primary Examiner* — Clinton Brooks
(74) *Attorney, Agent, or Firm* — Bruce Bradford

(57) ABSTRACT

A process for making a fluorinated olefin having the step of dehydrochlorinating a hydrochlorofluorocarbon having at least one hydrogen atom and at least one chlorine atom on adjacent carbon atoms, preferably carried out in the presence of a catalyst selected from the group consisting of (i) one or more metal halides, (ii) one or more halogenated metal oxides, (iii) one or more zero-valent metals/metal alloys, (iv) a combination of two or more of the foregoing.

23 Claims, No Drawings

PREPARATION OF FLUORINATED OLEFINS VIA CATALYTIC DEHYDROHALOGENATION OF HALOGENATED HYDROCARBONS

CROSS REFERENCE TO RELATED APPLICATIONS

This application claims priority to, and incorporates by reference, U.S. Provisional Application No. 60/958,468, filed Jul. 6, 2007.

BACKGROUND OF THE INVENTION

1. Field of the Invention

The present invention relates to the dehydrohalogenation of a halogen-containing compound. The present invention further relates to the dehydrochlorination of a hydrochlorofluorocarbon to a fluorinated olefin.

2. Description of the Related Art

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power cycle working fluids. However, CFCs have proven to be detrimental to the Earth's ozone layer. Conventional substitutes for CFCs include hydrofluorocarbons (HFCs); however, these compounds have been found to contribute to global warming. For these reasons, there is a worldwide effort to develop new compounds that are environmentally benign.

Partly or fully fluorinated olefins, including hydrofluoroolefins, (collectively referred to hereinafter as fluorinated olefins) are potential replacements for HFCs and CFCs. They can be used in some of the aforementioned applications and can also be used as feedstock monomers to synthesize fluoropolymers and other macromolecular compounds.

Various methods for producing certain fluorinated olefins are known, including those involving the dehydrochlorination of hydrochlorofluorocarbons. For example, U.S. patent application Ser. No. 11/619,592 discloses a method for preparing 2,3,3,3-tetrafluoropropene (1234yf) via dehydrochlorination of 1,1,1,2-tetrafluoro-2-chloropropane (244bb) with the aid of a catalyst. The 244bb reactant can be prepared through liquid phase or gas phase catalytic fluorination of 1,1,1-trifluoro-2-chloropropene (1233xf) with HF and 1233xf, in turn, can be made via gas phase fluorination of $CCl_2=CClCH_2Cl$ (1,1,2,3-tetrachloropropene) with HF. The '592 application also teaches the use of a carbon- and/or metal-based catalyst for the conversion of 244bb to 1234yf. Depending on the reaction conditions, the conversion of 244bb could be as high as 98%, but has a selectivity for 1234yf of only 69% to 86%. Thus, there remains a need to develop a commercially viable catalyst that not only is active, but also is more selective for 1234yf However, the conversion of a hydrochlorofluorocarbon to a fluorinated olefin by conventional methods is problematic because by-products often form and undergo a competing dehydrofluorination reaction. Hence, it would be advantageous to develop a catalyst system that can suppress undesirable dehydrofluorination reactions, so that single-pass productivity and yield of the desired fluorinated olefin can be increased.

SUMMARY OF THE INVENTION

According to the present invention, provided a process for making a fluorinated olefin via dehydrochlorination of a hydrochlorofluorocarbon having at least one hydrogen atom and at least one chlorine atom on adjacent carbon atoms. The dehydrochlorination is carried out in the presence of a catalyst selected from the group consisting of (i) one or more metal halides, (ii) one or more halogenated metal oxides, (iii) one or more zero-valent metals/metal alloys, and (iv) a combination of two or more of the foregoing. Preferred fluorinated olefin products are the following: 2,3,3,3-tetrafluoropropene (1234yf), 1,3,3,3-tetrafluoropropene (trans/cis-1234ze), 1,2,3,3,3-pentafluoropropene (Z/E-1255ye), 1,1,3,3,3-pentafluoropropene (1225zc), and 1,1,2,3,3,3-hexafluoropropene (1216).

DETAILED DESCRIPTION OF THE INVENTION

In the present invention, a hydrochlorofluorocarbon having at least one hydrogen and at least one chlorine on adjacent carbons is dehydrochlorinated in the presence of a catalyst to form a product having a fluorinated olefin therein. Table 1 sets forth examples of fluorinated olefins and precursor hydrochlorofluorocarbons from which they can be obtained (i.e., hydrochlorofluorocarbon in left column and corresponding fluorinated olefin in the right column).

TABLE 1

| Hydrochlorofluorocarbon | Fluorinated olefin(s) |
|---|---|
| chlorotetrafluoropropane | tetrafluoropropene |
| chloropentafluoropropane | pentafluoropropene |
| chlorohexafluoropropane | hexafluoropropene |
| 1,1,1,2-tetrafluoro-2-chloropropane $CF_3CFClCH_3$ (244bb) | 2,3,3,3-tetrafluoropropene $CF_3CF=CH_2$ (1234yf) |
| 1,1,1,2-tetrafluoro-3-chloropropane $CF_3CHFCH_2Cl$ (244eb) | 2,3,3,3-tetrafluoropropene $CF_3CF=CH_2$ (1234yf) |
| 1,1,1,3-tetrafluoro-3-chloropropane $CF_3CH_2CHFCl$ (244fa) | 1,3,3,3-tetrafluoropropene $CF_3CH=CHF$ (trans/cis-1234ze) |
| 1,1,1,3-tetrafluoro-2-chloropropane $CF_3CHClCH_2F$ (244db) | 1,3,3,3-tetrafluoropropene $CF_3CH=CHF$ (trans/cis-1234ze) |
| 1,1,1,2,3-pentafluoro-2-chloropropane $CF_3CFClCHF_2$ (235bb) | 1,2,3,3,3-pentafluoropropene $CF_3CF=CHF$ (Z/E-1225ye) |
| 1,1,1,2,3-pentafluoro-3-chloropropane $CF_3CHFCHFCl$ (235ea) | 1,2,3,3,3-pentafluoropropene $CF_3CF=CHF$ (Z/E-1225ye) |
| 1,1,1,3,3-pentafluoro-3-chloropropane $CF_3CH_2CF_2Cl$ (235fa) | 1,1,3,3,3-pentafluoropropene $CF_3CH=CF_2$ (1225zc) |
| 1,1,1,3,3-pentafluoro-2-chloropropane $CF_3CHClCHF_2$ (235da) | 1,1,3,3,3-pentafluoropropene $CF_3CH=CF_2$ (1225zc) |
| 1,1,1,2,3,3-hexafluoro-2-chloropropane $CF_3CFClCHF_2$ (226ba) | 1,1,2,3,3,3-hexafluoropropene $CF_3CF=CF_2$ (1216) |
| 1,1,1,2,3,3-hexafluoro-3-chloropropane $CF_3CHFCF_2Cl$ (226ea) | 1,1,2,3,3,3-hexafluoropropene $CF_3CF=CF_2$ (1216) |

In the process of the present invention, selected catalysts are employed to enhance the selectivity and/or conversion of hydrochlorofluorocarbons to fluorinated olefins. The catalysts are more selective for the dehydrochlorination reaction, which produces fluorinated olefin, than for the competing dehydrofluorination side reaction, which produces the undesirable byproduct chlorine-containing olefin.

There are three preferred classes of catalysts useful in the present invention: (i) metal halides, (ii) halogenated metal oxides, and (iii) zero-valent metals/metal alloys.

The first class of catalysts is metal halides, preferably mono-, bi-, and tri-valent metal halides and their mixtures/combinations, and more preferably mono- and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. The catalyst may be supported or unsupported. A preferred catalyst is a $CsCl/MgF_2$ combination. A particularly preferred catalyst is a $CsCl/MgF_2$ combination wherein CsCl is present in an amount of about 5.0 to about 50 wt % based on the total weight of the catalyst.

The second class of catalysts is halogenated metal oxides, preferably halogenated mono-, bi-, and tri-valent metal oxides and their mixtures/combinations, and more preferably halogenated mono- and bi-valent metal oxides and their mixtures/combinations. Component metals include, but are not limited to, Cr3+, Fe3+, $Mg^{2+}$, Ca2+, $Ni^{2+}$, Zn2+, Pd2+, $Li^+$, $Na^+$, $K^+$, and $Cs^+$. Halogenation treatments can include any of those known in the prior art, particularly those that employ HF, $F_2$, HCl, $Cl_2$, HBr, $Br_2$, HI, and $I_2$ as the halogenation source. Examples of useful halogenated mono- and bi-valent metal oxides include, but are not limited to, fluorinated or chlorinated MgO, fluorinated or chlorinated CaO, fluorinated or chlorinated $Li_2O$, fluorinated or chlorinated $Na_2O$, fluorinated or chlorinated $K_2O$, and fluorinated or chlorinated $Cs_2O$. The catalyst may be supported or unsupported.

The third class of catalysts is neutral (i.e., zero valent) metals, metal alloys, and their mixtures. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

In addition to the fluorinated olefin, i.e., the hydrofluorocarbon or fluorocarbon, the product mixture may also have unconverted hydrochlorofluorocarbon and hydrogen chloride.

Enhanced or improved selectivity for the target product is an important feature of the present invention. The dehydrochlorination reaction is preferably carried out at a selectivity of at least about 50%, more preferably at least about 70%, and most preferably at least about 80%. Conversion is preferably about 25% or more and most preferably about 40% or more.

Dehydrochlorination may be carried out at a temperature range of about 200° C. to about 800° C., preferably from about 300° C. to about 600° C., and more preferably from about 400° C. to about 500° C. in the presence of a catalyst. It is contemplated that a variety of reaction pressures may be used, such as superatmospheric, atmospheric, and subatmospheric. Atmospheric pressure is preferred.

Dehydrochlorination may optionally be carried out in presence or absence of an oxidizing agent. Useful examples of oxidizing agents include, but are not limited to, oxygen and carbon dioxide. Use of an oxidizing agent can extend the life of the catalyst. The oxidizing agent can be pure or diluted with an inert gas such as nitrogen before being introduced into reactor. The level of oxidizing agent is generally from about 1% to about 10% by volume and preferably from about 2% to 5% by volume based on the volume of the organic feed.

It may also be advantageous to periodically regenerate the catalyst after prolonged use while in place in the reactor. Regeneration of the catalyst may be accomplished by any means known in the art. One method is by passing oxygen or oxygen diluted with nitrogen over the catalyst at temperatures of about 200° C. to about 600° C. (preferably about 350° C. to about 450° C.) for about 0.5 hour to about 3 days followed by either halogenation treatment at temperatures of about 25° C. to about 400° C. (preferably about 200° C. to about 350° C.) for halogenated metal oxide catalysts and metal halide ones or reduction treatment at temperatures of about 100° C. to about 600° C. (preferably about 200° C. to about 350° C.) for metal catalysts.

Dehydrochlorination is preferably carried out in a corrosion-resistant reaction vessel. Examples of corrosion-resistant materials are Hastelloy, Inconel, Monel and fluoropolymer linings. The vessel may have a fixed or a fluidized catalyst bed. If desired, inert gases such as nitrogen or argon may be employed in the reactor during operation.

EXAMPLES

The following are examples of the present invention and are not to be construed as limiting.

Example 1

244bb Dehydrohalogenation Over Metal Fluoride and Fluorinated Metal Oxide Catalysts A series of mono-, bi-, and tri-valent metal fluorides and fluorinated bi- and tri-valent metal oxides were used as dehydrohalogenation catalysts. Approximately 20 cc of catalyst pellets was used in a typical run. A mixture containing 97.2 wt. % 244bb and 2.0 wt. % 1233xf was passed through the catalyst bed at a rate of 6 g/h at a temperature that ranged from 200° C. to 600° C. The temperatures at the bottom of catalyst bed and at the top of catalyst bed were measured.

As shown in Table 2, NaF, $MgF_2$, $CaF_2$, and fluorinated MgO were able to provide a selectivity to 1234yf higher than 80%, while $FeF_3$ and fluorinated $Cr_2O_3$ exhibited a selectivity to 1233xf higher than 80%. Selectivity is based on mole percent. These results indicate that mono- and bi-valent metal halides as well as halogenated mono- and bi-valent metal oxides are more favorable than their trivalent counterparts as catalysts for 244bb dehydrochlorination. Among NaF, $MgF_2$, $CaF_2$, and fluorinated MgO, $MgF_2$ exhibited the best performance; it provided a conversion of 244bb above 50% and a selectivity to 1234yf above 85% after 8 h (hours) on stream.

TABLE 2

| | (Dehydrohalogenation of 244bb over various mono-, bi-, and tri-valent metal fluorides and fluorinated bi- and tri-valent metal oxides*) | | | | | |
|---|---|---|---|---|---|---|
| Catalyst | Temp. Bottom-Top (° C.) | t (h) | Conversion 244bb (%) | Selectivity 1234yf (%) | Selectivity 1233xf (%) | Selectivity Unknowns (%) |
| NaF | 450-554 | 1 | 24.8 | 92.2 | | 7.8 |
| | 450-553 | 2 | 22.3 | 90.3 | | 9.7 |
| | 450-553 | 3 | 19.6 | 89.6 | | 10.4 |
| | 450-553 | 4 | 15.6 | 89.1 | | 10.9 |
| | 450-553 | 5 | 12.6 | 87.4 | | 12.6 |
| fluorinated MgO | 450-517 | 1 | 25.3 | 94.6 | | 5.4 |
| | 450-517 | 2 | 26.5 | 96.0 | | 4.0 |

TABLE 2-continued (Dehydrohalogenation of 244bb over various mono-, bi-, and tri-valent metal fluorides and fluorinated bi- and tri-valent metal oxides*)

| Catalyst | Temp. Bottom-Top (° C.) | t (h) | Conversion 244bb (%) | Selectivity 1234yf (%) | Selectivity 1233xf (%) | Selectivity Unknowns (%) |
|---|---|---|---|---|---|---|
|  | 450-518 | 3 | 25.8 | 96.8 |  | 3.2 |
|  | 450-518 | 4 | 25.4 | 97.1 |  | 2.9 |
|  | 450-516 | 5 | 26.6 | 97.3 |  | 2.7 |
|  | 450-516 | 6 | 26.3 | 97.5 |  | 2.5 |
| $MgF_2$ | 475-506 | 1 | 48.2 | 76.9 | 17.7 | 5.4 |
|  | 475-509 | 2 | 52.9 | 79.8 | 14.6 | 5.6 |
|  | 475-509 | 3 | 53.3 | 80.7 | 12.9 | 6.4 |
|  | 475-507 | 4 | 52.4 | 81.4 | 11.9 | 6.7 |
|  | 475-509 | 5 | 54.2 | 83.0 | 10.9 | 6.1 |
|  | 475-510 | 6 | 54.1 | 83.6 | 10.2 | 6.2 |
|  | 475-508 | 7 | 54.7 | 84.7 | 9.6 | 5.7 |
|  | 475-509 | 8 | 53.7 | 85.4 | 9.2 | 5.4 |
|  | 475-510 | 9 | 54.9 | 86.0 | 8.6 | 5.5 |
|  | 475-509 | 10 | 53.5 | 86.7 | 8.2 | 5.1 |
| $CaF_2$ | 450-511 | 1 | 7.0 | 76.8 |  | 23.2 |
|  | 450-510 | 2 | 7.3 | 80.2 |  | 19.8 |
| Fluorinated $Cr_2O_3$ | 250-317 | 1 | 95.3 | 6.2 | 92.6 | 1.2 |
|  | 250-316 | 2 | 55.0 | 8.0 | 89.2 | 2.8 |
| $FeF_3$ | 350-385 | 1 | 90.4 | 10.9 | 88.7 | 0.4 |
|  | 350-385 | 2 | 84.7 | 11.0 | 88.5 | 0.5 |

*Reaction conditions: 20 ml of catalyst, 6 g-organic/h, 97.2% 244bb/2.0% 1233xf, 1 atm Example 2

244bb Dehydrohalogenation Over Alkaline Metal Chloride-Doped $MgF_2$ Catalysts

A series of alkaline metal chlorides were investigated as an additive to $MgF_2$ with a purpose of improving the selectivity to 1234yf. For comparison purpose, the results obtained over $MgF_2$ catalyst were also reported. Approximately 20 cc of catalyst pellets was used in a typical run. A mixture containing 97.2 wt. % 244bb and 2.0 wt. % 1233xf was passed through catalyst bed at a rate of 6 g/h (grams/hour) at a temperature that ranged from 470° C. to 520° C. The temperatures at the bottom of catalyst bed and at the top of catalyst bed were measured.

As shown in Table 3, the $MgF_2$ provided a 244bb conversion of 53-55%, a 1234yf selectivity of 80-87%, and a 1233xf selectivity of 8-15%; the 10% $LiCl/MgF_2$ provided a 244bb conversion below 45%, a 1234yf selectivity of about 90%, and a 1233xf selectivity of about 5%; the 10% $KCl/MgF_2$ provided a 244bb conversion below 50%, a 1234yf selectivity of about 96%, and a 1233xf selectivity of about 1%; and the 10% $CsCl/MgF_2$ provided a 244bb conversion of 50-52%, a 1234yf selectivity of about 97%, and essentially no formation of 1233xf. CsCl exhibited the best results, while the 10% $CsCl/MgF_2$ catalyst provided activity comparable to $MgF_2$ and the highest 1234yf selectivity while generating no 1233xf.

TABLE 3

(Reactivity of $MgF_2$ and alkaline metal chloride-doped $MgF_2$ catalysts during 244bb dehydrohalogenation*)

| Catalyst | Temp. Bottom-Top (°) | t (h) | Conversion 244bb (%) | Selectivity 1234yf (%) | Selectivity 1233xf (%) | Selectivity, Unknowns (%) |
|---|---|---|---|---|---|---|
| $MgF_2$ | 475-506 | 1 | 48.2 | 76.9 | 17.7 | 5.4 |
|  | 475-509 | 2 | 52.9 | 79.8 | 14.6 | 5.6 |
|  | 475-509 | 3 | 53.3 | 80.7 | 12.9 | 6.4 |
|  | 475-507 | 4 | 52.4 | 81.4 | 11.9 | 6.7 |
|  | 475-509 | 5 | 54.2 | 83.0 | 10.9 | 6.1 |
|  | 475-510 | 6 | 54.1 | 83.6 | 10.2 | 6.2 |
|  | 475-508 | 7 | 54.7 | 84.7 | 9.6 | 5.7 |
|  | 475-509 | 8 | 53.7 | 85.4 | 9.2 | 5.4 |
|  | 475-510 | 9 | 54.9 | 86.0 | 8.6 | 5.5 |
|  | 475-509 | 10 | 53.5 | 86.7 | 8.2 | 5.1 |
| 10 wt % $LiCl/MgF_2$ | 475-490 | 1 | 29.4 | 89.1 | 5.3 | 5.6 |
|  | 475-506 | 2 | 38.8 | 89.6 | 5.3 | 5.0 |
|  | 475-505 | 3 | 40.4 | 89.9 | 5.2 | 4.9 |
|  | 475-507 | 4 | 42.9 | 90.5 | 4.8 | 4.7 |
| 10 wt % $KCl/MgF_2$ | 475-514 | 1 | 38.3 | 95.1 | 0.9 | 4.0 |
|  | 475-515 | 3 | 47.2 | 95.6 | 0.8 | 3.6 |
|  | 475-515 | 5 | 47.5 | 95.8 | 0.7 | 3.5 |
|  | 475-509 | 6 | 43.7 | 95.8 | 0.6 | 3.5 |
|  | 475-514 | 7 | 47.1 | 95.8 | 0.7 | 3.5 |

TABLE 3-continued (Reactivity of MgF$_2$ and alkaline metal chloride-doped MgF$_2$ catalysts during 244bb dehydrohalogenation*)

| Catalyst | Temp. Bottom-Top (°) | t (h) | Conversion 244bb (%) | Selectivity 1234yf (%) | Selectivity 1233xf (%) | Selectivity, Unknowns (%) |
|---|---|---|---|---|---|---|
| 10 wt % CsCl/MgF$_2$ | 475-511 | 1 | 49.6 | 96.9 | | 3.1 |
| | 475-510 | 2 | 51.2 | 97.0 | | 3.0 |
| | 475-511 | 3 | 51.8 | 96.9 | | 3.1 |
| | 475-508 | 4 | 50.4 | 96.9 | | 3.1 |
| | 475-510 | 5 | 51.4 | 97.0 | | 3.0 |

*Reaction conditions: 20 ml of catalyst, 6 g-organic/h, 97.2% 244bb/2.0% 1233xf, 1 atm

Example 3

244bb Dehydrohalogenation Over CsCl/MgF$_2$ Catalysts

A series of CsCl/MgF$_2$ catalysts with different loadings of CsCl were investigated with a purpose of optimizing CsCl loading. 20 cc of catalyst pellets was used in a typical run. A mixture containing 97.2 wt. % 244bb and 2.0 wt. % 1233xf was passed through the catalyst bed at a rate of 6 g/h at a temperature that ranged from 470° C. to 520° C. The temperatures at the top and bottom of the catalyst bed were measured. As shown in Table 4, the selectivity to 1233xf decreased with increasing CsCl loading from 0.0 to 5.0 wt %, and no 1233xf was formed over catalysts with CsCl loadings≥7.5 wt % based on the total weight of the catalyst.

TABLE 4

(Effect of CsCl loading on the performance of CsCl/MgF$_2$ catalysts during 244bb dehydrohalogenation*)

| CsCl loading (wt. %) | Temp. Bottom-Top (°) | t (h) | Conversion 244b (%) | Selectivity 1234yf (%) | Selectivity 1233xf (%) | Selectivity Unknowns (%) |
|---|---|---|---|---|---|---|
| 0.0 | 475-506 | 1 | 48.2 | 76.9 | 17.7 | 5.4 |
| | 475-509 | 2 | 52.9 | 79.8 | 14.6 | 5.6 |
| | 475-509 | 3 | 53.3 | 80.7 | 12.9 | 6.4 |
| | 475-507 | 4 | 52.4 | 81.4 | 11.9 | 6.7 |
| | 475-509 | 5 | 54.2 | 83.0 | 10.9 | 6.1 |
| | 475-510 | 6 | 54.1 | 83.6 | 10.2 | 6.2 |
| | 475-508 | 7 | 54.7 | 84.7 | 9.6 | 5.7 |
| | 475-509 | 8 | 53.7 | 85.4 | 9.2 | 5.4 |
| | 475-510 | 9 | 54.9 | 86.0 | 8.6 | 5.5 |
| | 475-509 | 10 | 53.5 | 86.7 | 8.2 | 5.1 |
| 2.5 | 500-514 | 1 | 48.4 | 88.7 | 5.2 | 6.1 |
| | 500-514 | 2 | 48.1 | 88.5 | 5.2 | 6.3 |
| | 500-514 | 3 | 49.5 | 89.1 | 5.0 | 5.9 |
| | 500-507 | 4 | 46.9 | 89.3 | 4.8 | 5.9 |
| | 500-509 | 5 | 48.5 | 89.9 | 4.6 | 5.5 |
| | 500-513 | 6 | 48.5 | 89.6 | 4.7 | 5.7 |
| | 500-514 | 7 | 49.6 | 89.9 | 4.6 | 5.5 |
| 5.0 | 490-510 | 1 | 49.0 | 94.8 | 0.5 | 4.7 |
| | 490-511 | 2 | 51.0 | 94.5 | 0.4 | 5.1 |
| | 490-510 | 3 | 49.2 | 95.3 | 0.5 | 4.2 |
| | 490-505 | 4 | 48.7 | 95.0 | 0.4 | 4.6 |
| | 490-507 | 6 | 49.8 | 95.4 | 0.4 | 4.2 |
| | 490-503 | 8 | 49.2 | 95.7 | 0.4 | 3.9 |
| 7.5 | 475-510 | 2 | 41.9 | 94.6 | | 5.4 |
| | 475-507 | 3 | 41.6 | 95.8 | | 4.2 |
| | 475-508 | 4 | 46.1 | 96.5 | | 3.5 |
| | 475-506 | 7 | 43.5 | 96.5 | | 3.5 |
| | 475-506 | 8 | 42.2 | 96.4 | | 3.6 |
| | 475-507 | 9 | 44.0 | 96.6 | | 3.4 |
| 10.0 | 475-511 | 1 | 49.6 | 96.9 | | 3.1 |
| | 475-510 | 2 | 51.2 | 97.0 | | 3.0 |
| | 475-511 | 3 | 51.8 | 96.9 | | 3.1 |
| | 475-508 | 4 | 50.4 | 96.9 | | 3.1 |
| | 475-510 | 5 | 51.4 | 97.0 | | 3.0 |

*Reaction conditions: 20 ml of catalyst, 6 g-organic/h, 97.2% 244bb/2.0% 1233xf, 1 atm

Example 4

244bb Dehydrohalogenation Over Non-Precious Metal-Doped MgF$_2$ Catalysts

A series of non-precious metals were investigated as additives to MgF$_2$ with a purpose of improving the selectivity to 1234yf. For comparison purposes, the results obtained over MgF$_2$ catalyst were also reported. Approximately 20 cc of catalyst pellets was used in a typical run. A mixture containing 97.2 wt. % 244bb and 2.0 wt. % 1233xf was passed through catalyst bed at a rate of 6 g/h at a temperature that ranged from 440 to 540° C. The temperatures at the top and bottom of the catalyst bed were measured.

As shown in Table 5, the addition of cobalt and especially nickel resulted in the decrease in the selectivity to 1233xf, while the addition of iron resulted in an increase in the selectivity to 1233xf. The 12 wt % Ni/MgF$_2$ catalyst provided a 1234yf selectivity of about 95% with a 1233xf selectivity of about 2%.

TABLE 5

(Reactivity of MgF$_2$ and metal-doped MgF$_2$ catalysts during 244bb dehydrohalogenation*)

| Catalyst | Temp. Bottom-Top (°) | t (h) | Conversion 244bb (%) | Selectivity 1234yf (%) | Selectivity 1233xf (%) | Selectivity, Unknowns (%) |
|---|---|---|---|---|---|---|
| MgF$_2$ | 450-529 | 1 | 53.5 | 69.0 | 26.0 | 5.0 |
| | 450-529 | 2 | 58.9 | 74.7 | 20.8 | 4.5 |

TABLE 5-continued (Reactivity of MgF$_2$ and metal-doped MgF$_2$ catalysts during 244bb dehydrohalogenation*)

| Catalyst | Temp. Bottom-Top (°) | t (h) | Conversion 244bb (%) | Selectivity 1234yf (%) | Selectivity 1233xf (%) | Selectivity, Unknowns (%) |
|---|---|---|---|---|---|---|
| | 450-528 | 3 | 60.4 | 77.9 | 17.4 | 4.7 |
| | 450-530 | 4 | 64.5 | 81.0 | 14.3 | 4.7 |
| | 450-529 | 5 | 61.4 | 82.4 | 12.9 | 4.8 |
| | 450-528 | 6 | 62.3 | 84.3 | 10.8 | 4.8 |
| | 450-529 | 7 | 63.7 | 85.3 | 9.7 | 5.0 |
| | 450-527 | 8 | 66.8 | 86.6 | 8.6 | 4.7 |
| | 450-526 | 9 | 64.3 | 87.0 | 8.2 | 4.8 |
| | 450-530 | 10 | 63.5 | 87.8 | 7.6 | 4.5 |
| | 450-528 | 11 | 63.8 | 88.2 | 7.2 | 4.6 |
| | 450-530 | 12 | 64.7 | 88.3 | 6.8 | 4.8 |
| | 450-528 | 13 | 64.1 | 88.6 | 6.6 | 4.8 |
| | 450-528 | 14 | 63.2 | 89.3 | 6.2 | 4.5 |
| 12 wt % Fe/MgF$_2$ | 450-525 | 1 | 71.2 | 53.4 | 41.7 | 4.9 |
| | 450-523 | 2 | 72.8 | 53.0 | 41.9 | 5.1 |
| 12 wt % Co/MgF$_2$ | 445-527 | 2 | 48.5 | 88.8 | 7.9 | 4.3 |
| | 445-528 | 3 | 58.0 | 90.1 | 6.7 | 3.2 |
| | 445-528 | 4 | 62.8 | 90.9 | 5.9 | 3.2 |
| | 445-527 | 5 | 66.6 | 91.5 | 5.2 | 3.3 |
| 12 wt % Ni/MgF$_2$ | 445-526 | 7 | 54.7 | 93.0 | 2.0 | 5.0 |
| | 445-527 | 8 | 53.2 | 93.4 | 2.1 | 4.5 |
| | 445-526 | 10 | 56.2 | 94.8 | 2.0 | 3.2 |
| | 445-526 | 11 | 58.6 | 94.5 | 2.0 | 3.4 |

*Reaction conditions: 20 ml of catalyst, 6 g-organic/h, 97.2% 244bb/2.0% 1233xf, 1 atm Example 5

244bb Dehydrohalogenation Over Metal and Metal Alloy Catalysts

A series of supported and unsupported metals as well as metal alloys were used as dehydrohalogenation catalysts. 20 cc of catalyst pellets or a 4 inch-long metal mesh roll was used in a typical run. A mixture containing 97.2 wt. % 244bb and 2.0 wt. % 1233xf was passed through a catalyst bed at a rate of 6 g/h at a temperature ranged from 420° C. to 480° C. The temperatures at the top and bottom of the catalyst bed were measured. As shown in Table 6, all the metal and metal alloy catalysts were active and extremely selective for 244bb dehydrochlorination (1234yf selectivity>95%) while generating no 1233xf. Compared to metal halide and/or halogenated metal oxide catalysts, the metal catalysts did not require as high an operating temperature.

TABLE 6

(reactivity of metal and metal alloys during 244bb dehydrohalogenation*)

| Catalyst | Temp. Bottom-Top (° C.) | t (h) | Conversion 244b (%) | Selectivity 1234yf (%) | Selectivity 1233xf (%) | Selectivity, Unknowns (%) |
|---|---|---|---|---|---|---|
| 5 wt % Pd/BaSO$_4$ | 450-478 | 1 | 43.6 | 95.3 | | 4.7 |
| | 450-476 | 2 | 30.5 | 94.6 | | 5.4 |
| | 450-478 | 3 | 30.1 | 92.9 | | 7.1 |
| | 450-475 | 4 | 29.6 | 95.1 | | 4.9 |
| | 450-481 | 5 | 31.1 | 94.8 | | 5.2 |
| Ni mesh | 425-473 | 1 | 45.8 | 96.9 | | 3.1 |
| | 425-473 | 2 | 45.5 | 97.3 | | 2.7 |
| | 425-473 | 3 | 44.8 | 97.8 | | 2.2 |
| | 425-473 | 4 | 43.7 | 97.9 | | 2.1 |
| | 425-473 | 5 | 42.1 | 97.9 | | 2.1 |
| | 425-473 | 6 | 40.5 | 98.0 | | 2.0 |
| | 425-472 | 7 | 39.5 | 98.0 | | 2.0 |
| | 425-473 | 8 | 38.6 | 98.0 | | 2.0 |
| | 425-473 | 9 | 38.6 | 98.9 | | 1.1 |
| | 425-474 | 10 | 39.2 | 98.1 | | 1.9 |
| Inconel 600 chips | 425-464 | 1 | 26.5 | 95.8 | | 4.2 |
| | 425-467 | 2 | 32.6 | 97.9 | | 2.1 |
| | 425-470 | 3 | 36.9 | 98.1 | | 1.9 |
| | 425-470 | 4 | 40.1 | 98.1 | | 1.9 |
| | 425-470 | 5 | 40.4 | 98.3 | | 1.7 |
| | 425-470 | 6 | 41.8 | 98.4 | | 1.6 |
| | 425-468 | 7 | 42.5 | 98.5 | | 1.5 |
| | 425-468 | 8 | 41.4 | 98.6 | | 1.4 |
| | 425-466 | 9 | 39.7 | 98.6 | | 1.4 |
| | 425-466 | 10 | 37.1 | 98.7 | | 1.3 |
| 20 cc Inconel 625 chips | 425-466 | 1 | 25.7 | 97.3 | | 2.7 |
| | 425-467 | 2 | 28.8 | 97.6 | | 2.4 |

TABLE 6-continued (reactivity of metal and metal alloys during 244bb dehydrohalogenation*)

| Catalyst | Temp. Bottom-Top (° C.) | t (h) | Conversion 244b (%) | Selectivity 1234yf (%) | Selectivity 1233xf (%) | Selectivity, Unknowns (%) |
|---|---|---|---|---|---|---|
|  | 425-467 | 4 | 33.4 | 97.9 |  | 2.1 |
|  | 425-459 | 6 | 33.8 | 98.0 |  | 2.0 |
|  | 425-465 | 8 | 36.2 | 98.1 |  | 1.9 |
|  | 425-463 | 10 | 36.8 | 98.1 |  | 1.9 |
|  | 425-465 | 12 | 38.0 | 98.2 |  | 1.8 |
|  | 425-465 | 14 | 37.7 | 98.2 |  | 1.8 |
|  | 425-462 | 16 | 39.1 | 99.1 |  | 0.9 |

*Reaction conditions: 20 ml of catalyst, 6 g-organic/h, 97.2% 244bb/2.0% 1233xf, 1 atm It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making 2,3,3,3-tetrafluoropropene, comprising:
    dehydrochlorinating 1,1,1,2-tetrafluoro-2-chloropropane in the presence of at least one catalyst selected from the group consisting of NaF, fluorinated MgO, $MgF_2$, $CaF_2$, fluorinated $Cr_2O_3$, $FeF_3$, LiCl with $MgF_2$, KCl with $MgF_2$, CsCl with $MgF_2$, CsCl, Fe with $MgF_2$, Co with $MgF_2$, Ni with $MgF_2$, Pd with $BaSO_4$, Ni, Inconel 600, and Inconel 625.

2. The process of claim 1 wherein dehydrochlorination is carried out at a temperature of from about 300 to about 600 ° C.

3. The process of claim 1 wherein dehydrochlorination is carried out at a temperature of from about 400 to about 500 ° C.

4. The process of claim 1, wherein the catalyst comprises NaF.

5. The process of claim 1, wherein the catalyst comprises fluorinated MgO.

6. The process of claim 1, wherein the catalyst comprises $MgF_2$.

7. The process of claim 1, wherein the catalyst comprises $CaF_2$.

8. The process of claim 1, wherein the catalyst comprises fluorinated $Cr_2O_3$.

9. The process of claim 1, wherein the catalyst comprises $FeF_3$.

10. The process of claim 1, wherein the catalyst comprises LiCl with $MgF_2$.

11. The process of claim 1, wherein the catalyst comprises KCl with $MgF_2$.

12. The process of claim 1, wherein the catalyst comprises CsCl with $MgF_2$.

13. The process of claim 1, wherein the catalyst comprises CsCl.

14. The process of claim 1, wherein the catalyst comprises Fe with $MgF_2$.

15. The process of claim 1, wherein the catalyst comprises Co with $MgF_2$.

16. The process of claim 1, wherein the catalyst comprises Ni with $MgF_2$.

17. The process of claim 1, wherein the catalyst comprises Pd with $BaSO_4$.

18. The process of claim 1, wherein the catalyst comprises Ni.

19. The process of claim 18, wherein the catalyst comprises Ni mesh.

20. The process of claim 1, wherein the catalyst comprises Inconel 600.

21. The process of claim 20, wherein the catalyst comprises Inconel 600 chips.

22. The process of claim 1, wherein the catalyst comprises Inconel 625.

23. The process of claim 22, wherein the catalyst comprises Inconel 625 chips.

* * * * *